US011536690B2

(12) United States Patent
Yanagimoto

(10) Patent No.: US 11,536,690 B2
(45) Date of Patent: Dec. 27, 2022

(54) ELECTRICAL CIRCUIT FOR ELECTROCHEMICAL MEASUREMENT AND MEASUREMENT DEVICE

(71) Applicant: PROVIGATE INC., Tokyo (JP)

(72) Inventor: Yoshiyuki Yanagimoto, Tokyo (JP)

(73) Assignee: PROVIGATE INC., Tokyo (JP)

(*) Notice: Subject to any disclaimer, the term of this patent is extended or adjusted under 35 U.S.C. 154(b) by 141 days.

(21) Appl. No.: 17/044,204

(22) PCT Filed: Mar. 25, 2019

(86) PCT No.: PCT/JP2019/012350
§ 371 (c)(1),
(2) Date: Mar. 1, 2021

(87) PCT Pub. No.: WO2019/188896
PCT Pub. Date: Oct. 3, 2019

(65) Prior Publication Data
US 2021/0293747 A1 Sep. 23, 2021

(30) Foreign Application Priority Data

Mar. 30, 2018 (JP) .............................. JP2018-066582

(51) Int. Cl.
*G01N 27/416* (2006.01)
*G01N 27/22* (2006.01)
*G01N 27/30* (2006.01)

(52) U.S. Cl.
CPC ....... *G01N 27/4161* (2013.01); *G01N 27/226* (2013.01); *G01N 27/228* (2013.01); *G01N 27/301* (2013.01)

(58) Field of Classification Search
CPC ............ G01N 27/4161; G01N 27/226; G01N 27/228; G01N 27/301; G01N 33/48707; G01N 27/48
See application file for complete search history.

(56) References Cited

U.S. PATENT DOCUMENTS 5,470,484 A * 11/1995 McNeel ................. G01N 33/18
324/439
6,228,237 B1 * 5/2001 Goumont ............... G01N 27/48
324/714

(Continued)

FOREIGN PATENT DOCUMENTS

JP S60-149960 A 8/1985
JP H07-209250 A 8/1995

(Continued)

OTHER PUBLICATIONS

Li et al., CMOS Electrochemical Instrumentation for Biosensor Microsystems: A Review. 2017, Sensors , 17, 74, (Year: 2017).*

(Continued)

*Primary Examiner* — Joshua L Allen
*Assistant Examiner* — Shizhi Qian
(74) *Attorney, Agent, or Firm* — McBee Moore & Vanik IP, LLC

(57) ABSTRACT

Provided is an electrical circuit for electrochemical measurement of a solution, said electrical circuit comprising: a voltage generation circuit; an operational amplifier that has an output (OUT), a non-inverting input (+IN), and an inverting input (−IN), wherein the output (OUT) is connected to a counter electrode (CE) in contact with the solution, the inverting input (−IN) is connected to a reference electrode (RE) in contact with the solution, and the non-inverting input (+IN) is connected to the voltage generation circuit; a capacitor that is connected between the output (OUT) and inverting input (−IN) and has a capacitance of 1 μF or greater; and a current measurement circuit that is connected to a working electrode (WE) in contact with the solution.

9 Claims, 10 Drawing Sheets

(56) References Cited

U.S. PATENT DOCUMENTS

2007/0080060 A1* 4/2007 Frey .................... G01R 19/252
                                                    204/406
2018/0059054 A1* 3/2018 Nishida .............. G01N 27/4163
2018/0372667 A1* 12/2018 Gupta ................... G01N 27/30

FOREIGN PATENT DOCUMENTS

| JP | H09-502527 A | 3/1997 |
| JP | H11-326279 A | 11/1999 |
| JP | 2017-51593 A | 3/2017 |

OTHER PUBLICATIONS

Velusamy V., Design, Development and Characterization of a Handheld Electrochemical Analyzer System, PhD thesis, University of Limerick, 2012 (Year: 2012).*
International Search Report of International Patent Application No. PCT/JP2019/012350 dated Jun. 18, 2019.

* cited by examiner

ELECTRICAL CIRCUIT FOR ELECTROCHEMICAL MEASUREMENT AND MEASUREMENT DEVICE

CROSS-REFERENCE TO RELATED APPLICATIONS

This application is the National Stage entry of International Application No. PCT/JP2019/012350, filed 25 Mar. 2019, which claims priority to Japan No. 2018-066582, filed 30 Mar. 2018.

TECHNICAL FIELD

The present disclosure relates to an electrical circuit for electrochemical measurement and a measurement device.

BACKGROUND OF THE INVENTION

In the electrochemical field, a chemical substance or a biological substance is detected or quantified by measuring an electric current flowing in a solution by a chemical reaction or a biochemical reaction in which a chemical substance or a biological substance in a solution occurs at or near an electrode surface. For such measurement, for example, a method such as three-electrode method is widely used.

The three-electrode method is a method in which a counter electrode, a reference electrode, and a working electrode are installed in a container, a predetermined potential difference is provided between the counter electrode and the working electrode, and a current flowing from the counter electrode to the working electrode is measured. Generally, when a substance such as a metal or a metal oxide enters an electrolytic solution, a potential difference called an interfacial potential occurs between the substance and the electrolytic solution. Taking this potential difference into consideration, when a voltage is applied between the counter electrode and the working electrode, current flows from the counter electrode, and the potential difference between the counter electrode and the solution may change. Due to this change in potential difference, the desired voltage may not be accurately applied to the solution. In the three-electrode method, in order to avoid this, the potential at the reference electrode can be measured, and the voltage applied to the counter electrode can be controlled so that the potential is determined to a desired value. There is also a feedback circuit that feeds back the measured potential at the reference electrode to the circuit that controls the counter electrode.

SUMMARY OF THE INVENTION

In one embodiment of the present disclosure, an electrical circuit to be used for an electrochemical measurement of a solution comprises:
a voltage generating circuit;
an operational amplifier having an output (OUT), a non-inverting input (+IN), and an inverting input (−IN), wherein the output (OUT) is configured to be connected to a first electrode in contact with the solution, wherein the inverting input (−IN) is configured to be connected to a second electrode in contact with the solution, and wherein the non-inverting input (+IN) is connected to the voltage generating circuit; and
a capacitor connected between the output (OUT) and the inverting input (−IN).

In some embodiments of the present disclosure an electrical circuit used for an electrochemical measurement of a solution is provided. The electrical circuit comprises: a voltage generating circuit; an operational amplifier having an output (OUT), a non-inverting input (+IN), and an inverting input (−IN), wherein the output (OUT) is configured to be connected to a counter electrode (CE) in contact with the solution, wherein the inverting input (−IN) is configured to be connected to a reference electrode (RE) in contact with the solution, and wherein the non-inverting input (+IN) is configured to be connected to the voltage generating circuit;
a capacitor connected between the output (OUT) and the inverting input (−IN); and
a current measuring circuit configured to be connected to a working electrode (WE) in contact with the solution.

In some embodiments of the present disclosure an electrical circuit used for an electrochemical measurement of a solution is provided. The electrical circuit comprises: an operational amplifier having an output (OUT), a non-inverting input (+IN), and an inverting input (−IN), wherein the output (OUT) is configured to be connected to a counter electrode (CE) in contact with the solution, and wherein the inverting input (−IN) is configured to be connected to a reference electrode (RE) in contact with the solution, wherein the non-inverting input (+IN) is configured to be connected to the voltage generating circuit;
a capacitor connected between the output (OUT) and the inverting input (−IN); and
a wiring configured to connect the working electrode (WE) in contact with the solution and the current measuring circuit.
The voltage generating circuit may be connected to the non-inverting input (+IN) of the operational amplifier. The current measurement circuit may be connected to a wiring configured to be connected to the working electrode (WE).

In another embodiment of the present disclosure an electrochemical measuring device (apparatus) for a solution is provided. The electrochemical measurement device comprises:
a counter electrode (CE) configured to contact the solution;
a reference electrode (RE) configured to contact the solution;
a working electrode (WE) configured to contact the solution;
a voltage generating circuit;
an operational amplifier having an output (OUT), a non-inverting input (+IN), and an inverting input (−IN), the operational amplifier being connected to the counter electrode (CE) at the output (OUT), the inverting input (−IN) at the reference electrode (RE), and the voltage generating circuit at the non-inverting input (+IN);
a capacitor being connected between the output (OUT) and the inverting input (−IN) of the operational amplifier; and
a current measuring circuit being connected to the working electrode (WE).

According to the present disclosure, potentially or by way of example, it is possible to reduce the influence of noise on measurement and to improve the measurement accuracy of minute currents generated by chemical reactions and biochemical reactions in electrochemical measurements in solution.

Figure 1:
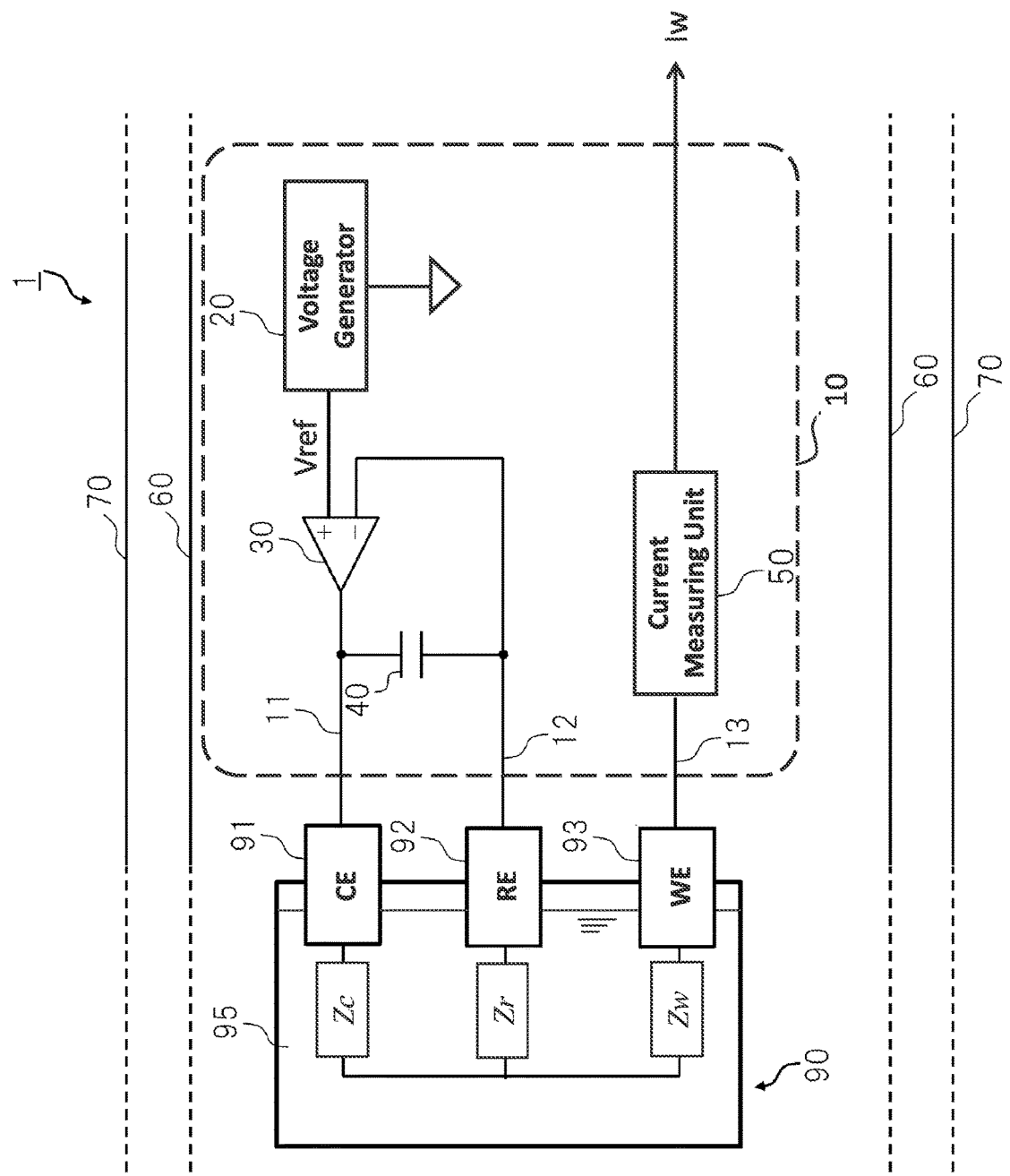
FIG. 1 illustrates a circuit block diagram showing an example of a configuration of a measurement device according to the first embodiment.

Generally, measurement systems which perform the electrical measurements are affected by noise. Noise sources include, for example, commercial power supplies, switching power supplies, clocks, external devices, electrostatic and communications radio waves, and the like. The sources of these noises are identified. These are not inherent in the measurement system as in the electrodes or the feedback loop described below, but exist outside the measurement system. Therefore, in the present disclosure, these are collectively referred to as "external noise".

The source of external noise is relatively easy to identify. Therefore, if the propagation path from the source of the noise to the measurement unit is cut off, it is possible to reduce the effect. For example, if the measuring system is covered with a shield, the effects of noise, static electricity, and communication radio waves propagating from external equipment can be greatly reduced. Further, the influence of noise caused by commercial power supply, switching power supply, clock, etc. entering the inside of the measuring device can be reduced by appropriately placing the ground of the measuring device. Alternatively, with the exception of static electricity and commercial power supplies, these noises can be reduced by a low-pass filter (LPF) or the like because of their high frequency. In addition, the frequency of commercial power supply is determined by the country and region to be 50 Hz or 60 Hz. Therefore, the averaging process in accordance with the period (e.g., averaging the data for 0.1 seconds, the signal of 50 Hz/60 Hz becomes zero), it is possible to further reduce the noise. Though the frequency of the static electricity is not fixed, the countermeasure can be sufficiently carried out by properly applying the shield.

On the other hand, in addition to external noise, in the measuring device, there is also noise such as thermal noise, shot noise, flicker noise (1/f noise). These noises, as a physical phenomenon, can not be reduced by proper arrangement of the shield or ground, because they are present inside the device or electrical or electronic elements in the measuring device. Further, these noises are present at low frequency, and thus may be difficult to reduce in the averaging process. In particular, flicker noise (1/f noise) is difficult to reduce in the averaging process since its noise power is increased at low frequencies.

In electrochemical measurements, a current flowing through the working electrode by a chemical reaction or a biochemical reaction is measured. When the concentration of the substance to be measured is low, the current flowing is very small. In such a case, if the noise is large, it may not be possible to quantify or even detect the substance to be measured. Even if quantification is possible, the quantified values may be extremely inaccurate.

The solution for electrochemical measurements may be a liquid taken from a living body. The solution may be a liquid itself taken from a living body, and may be a liquid taken from a human body. Liquid taken from a living body may be purified, diluted, mixed with other liquid, or otherwise treated liquid, or a biologically derived liquid. The solution for electrochemical measurement may be a body fluid. The body fluid may be intracellular fluid (ICF) or extracellular fluid (ECF). The body fluid may be lymph fluid, tissue fluid such as interstitial fluid, intercellular fluid, or interstitial fluid, and may be body cavity fluid, serosal fluid, pleural fluid, ascites fluid, effusions, cerebrospinal fluid, joint fluid (synovial fluid), or aqueous humor of eye (aqueous humor). The body fluid may be digestive fluid such as saliva, gastric juice, bile, pancreatic juice, intestinal fluid, etc., and may be sweat, tears, nasal mucus, urine, semen, vaginal fluid, amniotic fluid, milk, etc. The solution may be a physiological buffer such as phosphate buffered saline (PBS) or N-tris (hydroxymethyl)methyl-2-aminoethanesulfonic acid buffer (TES), containing a substance to be measured.

The solution may contain a substance to be measured. For example, the solution may be tears and the substance to be measured may be glycoalbumin contained in tears. Alternatively, the substance to be measured may be glucose in blood or serum, albumin, glycoalbumin, uric acid, glycated hemoglobin, glucose in interstitial fluid, glucose in tears, albumin, urinary albumin, glucose, etc. The solution should not particularly be limited as long as the substance to be measured is contained.

The electrochemical measurement method may be an amperometric method during electrolysis. In the measurement methods using electrolysis, the amperometry may measure the current value when the potential is kept constant, or the voltammetry may measure the variation of the current amount when the potential is varied. The electrochemical measurement method may be a three-electrode method.

The voltage generating circuit (voltage generator, the voltage generating unit) may include a power supply, or may be configured to convert the voltage from a power supply provided at its outside to a desired voltage. It may include a circuit for dividing the power supply voltage, or it may include an integrated circuit (IC) capable of generating a desired voltage. The voltage generating circuit may be configured to have a low-pass filter circuit and a buffer circuit.

In the present disclosure, "connection" means electrical connection, unless otherwise stated. A "connection" may be a direct connection, i.e., a connection in which the elements, etc. to be connected do not substantially mediate other electrical or electronic elements, etc. therebetween, or may be an indirect connection, i.e., a connection between the elements, etc. to be connected, i.e., via other electrical or electronic elements, etc., as long as the invention or embodiment included in the disclosure functions. For example, the output of the operational amplifier (OUT) and the counter electrode (CE) may be directly connected, or a resistor of, for example, 100Ω (ohms) may be connected in series between the output of the operational amplifier (OUT) and the counter electrode (CE) so as not to damage the electronic elements in the circuit by making a connection error. For example, the output of the operational amplifier may not be directly connected to the counter electrode. In some embodiments, an amplifier circuit or an attenuation circuit may further be connected in the subsequent stage. In another embodiment, multiple stages of operational amplifiers may be used for connection. In some embodiments, a protective resistor may be placed in series to form the connection.

In some embodiments, the capacitor is connected between the output (OUT) and the inverting input (−IN). The capacitor may be connected to the output (OUT) at one end and to the inverting input (−IN) at the other end.

In some embodiments, the capacitor may have a capacitance of 1 µF or greater. In another embodiment, the capacitor may have a capacitance greater than 1 µF. The capacitance of the capacitor may be greater than or equal to 2 µF, 3 µF, 4 µF, 5 µF, 6 µF, 7 µF, 8 µF, 9 µF, or 10 µF, or may be greater than any value thereof. The capacitance of the capacitor may be greater than or equal to 10 µF, 20 µF, 30 µF, 40 µF, 50 µF, 60 µF, 70 µF, 80 µF, 90 µF, or 100 µF, or may be greater than any value thereof.

In some embodiments, the capacitance of the capacitor may be greater than the capacitance of the equivalent circuit at the interface of the counter electrode under measurement. In some embodiments, the capacitor may be a noise reduction capacitor. The contact area of the electrode with the solution may be less than or equal to 100 square millimeters. The capacitance of the electrode interface may generally be about 10 µF or smaller. The thickness of the electric double layer may be as small as 1 nm or greater than this. As an example, the capacitance at the electrode interface may be $C=\varepsilon S/D=70$ µF (as the relative permittivity of water $\varepsilon=80$). Alternatively, in another example, it may be on the order of several µF. Along with these, if the capacitance of the capacitor is 10 µF, noise can sufficiently be reduced. Further, if the capacitance of the capacitor is 100 µF, noise can be further reduced. For example, if the electrode area is further smaller, the capacitance of the capacitor may be 0.1 µF.

In the present disclosure, there is no theoretical upper limit on the capacitance of the capacitor, but in practice, an upper limit may be provided. The capacitance of the capacitor may be smaller than or equal to 100 mF, 10 mF, 1 mF, 500 µF, 400 µF, 300 µF, 200 µF, 100 µF, or may be smaller than any value thereof. The capacitance of the capacitor may be 350 µF or 330 µF.

The capacitor may be a ceramic capacitor. The capacitor may be configured by combining two or more capacitors. For example, two electrolytic capacitors may be connected in series in opposite directions. The capacitor may or may not have polarity. Non-polar capacitors are useful when the voltage applied to them may vary between positive and negative.

The counter electrode, the reference electrode, and the working electrode may be referred to as an electrode, and may be referred to as a counter electrode, a reference electrode, and a working electrode, respectively. The working electrode, at least on a surface in contact with the solution, may be formed of a metal such as platinum (Pt), gold (Au), silver (Ag), or copper (Cu), may be a carbon electrode including carbon nanotubes, graphene, diamond, or the like, may be a metal oxide such as tantalum oxide, or may be a conductive polymer. The counter electrode, at least on a surface in contact with the solution, may be formed of a metal such as platinum (Pt), gold (Au), silver (Ag), or copper (Cu), or may be formed of a carbon electrode, a conductive polymer, or the like. The reference electrode, at least on a surface in contact with the solution, may be formed of at least silver chloride (Ag/AgCl), a saturated KCl salt bridge, mercury (Hg), mercury chloride (HgCl), a standard hydrogen electrode, or the like. These materials are merely examples and do not specify the material of the electrode in the present disclosure.

Current measuring circuit may have a current-voltage conversion circuit. In some embodiments, the current measurement circuit may be configured with a current-voltage conversion circuit and a voltage measurement circuit connected in series. In some embodiments, the voltage measurement circuit may be an A/D converter.

Generally, in an electric circuit, a point where a plurality of circuit elements or wires are connected is called a nodal point or a node, often represented by a point of black circle However, in the present disclosure, the nodal point or node as well as locations such as wiring sections that can be treated as substantially the same potential for circuit function, with the exception of the electrical and electronic circuitry or elements explicitly shown, are called a node.

Hereinafter, embodiments of the present invention will be described in detail with reference to the drawings. In all the drawings for explaining the embodiments, the same portions are denoted by the same reference numerals in principle, and repetitive descriptions thereof are omitted.

FIRST EMBODIMENT

<Configuration of Measurement Device>

FIG. 1 illustrates a circuit block diagram showing a configuration of a measurement device according to a first embodiment of the present disclosure. The measuring device 1 is an apparatus for performing electrochemical measurement of a solution. The measuring device 1 can also detect and quantify the substance to be measured in the solution. The measuring device 1 shown in FIG. 1 comprises an electric circuit 10, a container 90 containing a solution, a counter electrode 91, a reference electrode 92, and a working electrode 93, arranged in the container 90 and in contact with the solution 95 at the time of measurement. Electric circuit 10 includes a voltage generating circuit (voltage generator, voltage generating unit) 20, an operational amplifier 30, a capacitor 40, a current measuring circuit (current measuring unit, a current measuring instrument) 50. The voltage generating circuit 20, the operational amplifier 30, the capacitor 40, the current measuring circuit 50 are in part or entirely formed on a substrate (not shown). In some embodiments, the substrate may be a substrate of a material such as paper phenol, glass epoxy, or the like.

The output of the voltage generating circuit 20 is connected to the non-inverting input (+IN) of the operational amplifier 30, and supplies a reference voltage Vref. The voltage generating circuit 20 supplies an output signal having the stable potential difference Vref with respect to the ground potential of the measuring device 1.

The output of the operational amplifier 30 (OUT) is connected to the counter electrode 91, and the inverting input (−IN) is connected to the reference electrode 92. The capacitor 40 is connected between the counter electrode 91 and the reference electrode 92, or between the output (OUT) and the inverting input (−IN) of the operational amplifier 30. In other words, the capacitor 40 is connected to the output of the operational amplifier 30 (OUT) and the counter electrode 91 at one end, and is connected to the inverting input (−IN) and the reference electrode 92 of the operational amplifier 30 at the other end.

The current measuring circuit 50 is connected to the working electrode 93 and receives the value of the current from the working electrode 93 and outputs an output signal to the outside of the electric circuit 10.

A substantially equipotential wiring section between the output (OUT) of the operational amplifier 30 and the capacitor 40, or between the output (OUT) of the operational amplifier 30, the capacitor 40, and the counter electrode 91 is referred to as a node (first node) 11. A substantially equipotential wiring section between the inverting input (−IN) of the operational amplifier 30 and the capacitor 40, or between the inverting input (−IN) of the operational amplifier 30, the capacitor 40 and the reference electrode 92 is referred to as a node (second node) 12. A substantially equipotential wiring section between the working electrode 93 and the current measuring circuit is referred to as a node (third node) 13.

In some embodiments, the container 90 containing the solution 95, the counter electrode 91, the reference electrode 92, and the working electrode 93 may be configured to be removed from the measuring device 1. The container 90 containing the solution 95, the counter electrode 91, the reference electrode 92, and the working electrode 93 may be configured to be disposable at each measurement, according to the frequency of use or according to the time interval. In some embodiments, the container 90 containing the solution, the counter electrode 91, the reference electrode 92, and the working electrode 93 may be fitted into the measurement device 1 such that the counter electrode 91, the reference electrode 92, and the working electrode 93 may be configured to form electrical contact with the first node 11, the second node 12, and the third node 13, respectively. In another embodiment, the container 90 containing the solution, the counter electrode 91, the reference electrode 92, and the working electrode 93 may be integrally formed or manufactured in the measuring device 1.

In FIG. 1, the measuring device 1 includes a shield 60. Shield 60 can reduce external noise. In FIG. 1, the shield 60 is disposed so as to surround the electric circuit 10, the container 90, the counter electrode 91, the reference electrode 92, and the working electrode 93, but the arrangement of the shield 60 is not limited thereto. The shield 60 may be disposed along or surrounding the second node 12.

The first node 11 to the third node 13 may be disposed on the substrate. The shield 60 may be made of a metal or a conductive material. The shield 60 may be connected to the ground potential of the measuring device 1. In some embodiments, each or all of the nodes connected to the counter electrode, the reference electrode and the working electrode may be formed in part by a coaxial cable (not shown). The inner conductor of the coaxial cable is connected to each electrode as a wiring of each node, and the outer conductor may be connected to the shield 60. If the node is physically long, the external noise picked up by the node can be reduced. In some embodiments, the coaxial cable may be configured to connect the electrical circuit and the electrodes via a removable connector (not shown). In the present disclosure, how the first node 11, the second node 12, and the third node 13 of the measurement apparatus 1 are connected to the counter electrode 91, the reference electrode 92, and the working electrode 93 is not limited.

In some embodiments, the wiring configured to be connected to the output (OUT) of the operational amplifier 30, the inverting input (−IN) of the operational amplifier 30, and the current measurement circuit 50 may be configured to be connected to the counter electrode 91 (CE), the reference electrode 92 (RE), and the working electrode 93 (WE) that are in contact with the solution during the electrochemical measurement, respectively. In some embodiments, the measuring device 1 and the electrical circuit path 10 may be configured such that the component including the electrical circuit and the component including the counter electrode (CE), the reference electrode (RE), and the working electrode (WE) are in contact or merged in a form of a mechanical fit or the like to form electrical contact with the respective wires of the counter electrode 91 (CE), the reference electrode 92 (RE), and the working electrode 93 (WE).

In some embodiments, the container 90 containing the solution 95 may be configured to be removal with respect to the measuring device 1 in a cartridge manner. The container 90 may have an inlet for introducing a solution 95 or other liquid. The container 90 may have an outlet for discharging the solution 95 and other liquids. Each of the inlet and the outlet may be one or plural, and may be configured as the same hole. In some embodiments, the counter electrode 91 (CE), the reference electrode 92 (RE), and the working electrode 93 (WE) may be secured to the container 90 and removably fixable to the container 90. In some embodiments, the container 90 may be configured to contain solution 95 in a substantially non-flowing state during measurement. In another embodiment, the container 90 may be configured as a channel.

Measurement device 1 shown in FIG. 1 comprises a housing 70. In some embodiments, the housing 70 may be configured to house or support container 90 and electrical circuit 10. The measuring device 1 may be a desktop type device or a portable type device.

In measuring, the solution 95 is flowed into or introduced into the container 90 from the introduction port or inlet (not shown).

The substance to be measured or the measurement object substance may be contained in the solution in advance, or may be mixed into the solution 95 after the solution containing no substance to be measured is introduced into the container 90, at a different timing. The timing at which the substance to be measured and the solution are mixed is not limited thereto. For example, in some embodiments, a solution 95 in which a substance to be measured is dissolved may be poured into the container 90 from a state in which the counter electrode 91, the reference electrode 92, and the working electrode 93 are not in contact with the solution 95, that is, from a dry state. In another embodiment, a solution containing no substance to be measured may be introduced into the container 90 to immerse the counter electrode 91, the reference electrode 92, and the working electrode 93, and be replaced by a solution in which the substance to be measured is dissolved after. In yet another embodiment, the counter electrode 91, the reference electrode 92, and the working electrode 93 may be immersed in a solution containing no substance to be measured, and the substance to be measured itself may be dissolved in the solution in the container 90. In yet another embodiment, the counter electrode 91, the reference electrode 92, and the working electrode 93 may be immersed in a solution containing no substance to be measured, and a sample to be measured in which the substance to be measured is mixed may be dissolved in the solution.

The introduced solution 95 contacts at least a portion of the surface of the counter electrode 91, the reference electrode 92, and the working electrode 93

When a voltage is provided from the voltage generator 20, a feedback loop is formed that returns from the output of the operational amplifier 30, via the first node 11, the counter electrode 91, the solution 95, the reference electrode 92, and the second node 12, back to the inverting input (−IN) of the operational amplifier 30. By the action of this feedback loop, the voltage of the counter electrode 91 is controlled so that the voltage transmitted from the reference electrode 92 to the second node 12 is equal to the reference voltage Vref. As the operational amplifier 30 is one component of the feedback circuit, another circuit component having similar functions may be used in another embodiment.

Capacitor 40 can reduce the effects of noise inherent in the components of the device, such as thermal noise, shot noise, flicker noise, and the like (hereinafter referred to as "physical noise").

In the feedback circuit as shown in FIG. 1, the physical noise is inherent in the components of the voltage generating circuit 20 and the operational amplifier 30. The physical noise inherent in the components of the voltage generating circuit 20 is superimposed on the reference voltage signal as voltage noise is input to the non-inverting input terminal of the operational amplifier 30 (+IN). Physical noise inherent in the operational amplifier 30 is present in both the inverting input (−IN) and the non-inverting input (+IN), but equivalently can be calculated as the sum is present concentrated on the non-inverting input (+IN) of the operational amplifier 30. The noise of the operational amplifier 30 is superimposed on the reference voltage signal. From these, the physical noise present at various locations can be considered as one noise summed on the non-inverting input (+IN) of the operational amplifier 30 superimposed on the reference voltage Vref. This is hereinafter also referred to as "integrated physical noise".

Here, physical properties and electrical properties of the interface between the electrode and the solution will be briefly described. The interface between the electrode and the solution is surrounded by complex phenomena. When AC voltage is applied to the interface, the corresponding current flows, so the impedance of the interface can be defined by its ratio. In the present disclosure, this is referred to as interface impedance. The ones that constitute the interfacial impedance are redox reactions and electric double layers. The oxidation reduction (redox) reaction generates the transfer of electrons between the solution and the electrode, whereby a direct current flows. The electric double layer is formed by ions that collect at the interface and does not generate transfer of electrons. However, when the potential of the electrode changes, the ion concentration distribution in the solution changes, and the state of the electron of the electrode changes accordingly, and this is detected as an alternating current. Therefore, electrically, the oxidation-reduction reaction can be expressed as a resistor, and the electric double layer can be expressed as a capacitor. Therefore, the interface impedance can be approximately expressed as a parallel circuit of these. In addition, at the interface, there are complex elements such as Warburg impedance dominated by the diffuse rate. However, since these are not factors that greatly affect the present disclosure, a description thereof will be omitted. The counter electrode 91, the reference electrode 92, and the working electrode 93 each have an interface impedance, and each can be approximately expressed as a parallel circuit of resistance and capacitance.

The integrated physical noise is amplified by the feedback loop. The mechanism will be described below. The amount of feedback from the operational amplifier output to the inverting input is determined by the impedance division Zw/(Zc+Zw) with the interface impedance Zc between the counter electrode 91 and the solution 95, and the interface impedance Zw between the working electrode 93 and the solution 95.

In practice, there is a path through the impedance Zr of the equivalent circuit at the interface of the reference electrode 92 and the solution 95. However, since the input impedance of the inverting input (−IN) of the operational amplifier 30 beyond that is sufficiently large, the impedance Zr at the reference electrode 92 may be considered not to affect the impedance division in the feedback path. Further, the input impedance of a general operational amplifier is sufficiently large compared to the value of Zc and Zw obtained realistically. Further, the input impedance of the current measuring circuit 50 may be considered sufficiently small. Again, the ammeter is required to have a low input impedance. For example, in the current measuring circuit 50 shown in FIG. 8, the current-voltage conversion circuit 51 has a virtual ground at the input unit, the input impedance may be regarded as zero.

Figure 9:
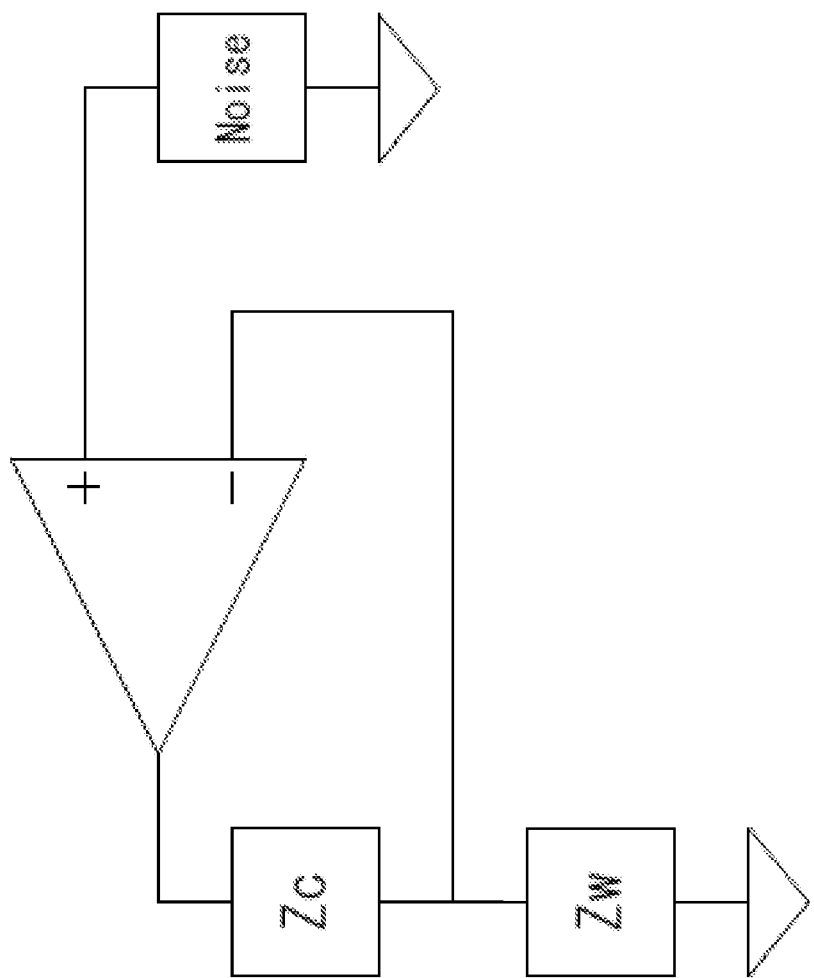
FIG. 9 illustrates a circuit block diagram for explaining a mechanism for a feedback circuit amplifying noise.

In FIG. 9 modeling only the operational amplifier 30, the equivalent impedances Zc, Zw of the counter electrode 91 and the working electrode 93, and the input of the current measuring circuit 50 serving as the virtual ground, the arrangement of the feedback circuit constitutes a typical non-inverting amplifier. Therefore, it can be considered that the physical noise integrated at the non-inverting input (+IN) of the operational amplifier 30 is amplified by (Zc+Zw)/Zw, and appears at the output of the operational amplifier 30, and then appears at the counter electrode 91 through the first node 11, as it is.

Electrochemical measurements, such as the three-electrode method, currents due to chemical or biochemical reactions by minute amounts of substances contained in the solution are measured. In order to obtain more current, it is effective to increase the contact area of the working electrode with the solution. Generally, the area of the working electrode is larger than the area of the counter electrode. When the contact area is large, the impedance of the interface becomes small, and the capacitance becomes large.

Hereinafter, the calculation will be specifically considered. For example, as measured in an example, the area of the working electrode was about 2.5 times the area of the counter electrode, and the equivalent circuits of the interface of the counter electrode, the reference electrode, and the working electrode were 35 MΩ//2.8 μF, 2 MΩ//1.4 μF, and 14 MΩ//7 μF, respectively. Here, "//" indicates that the left and right elements are connected in parallel.

Considering the speed of the chemical reaction, the time required for the measurement is about 0.1 second to about 1 minute, and the frequency is in the range of about 0.01 Hz to 10 Hz. In that frequency band, the impedance is substantially proportional to the inverse of the capacitance, since the capacitance is dominant in the equivalent circuit of the interface. If the input impedance of the inverting input (−IN) of the operational amplifier 30 is sufficiently large, Zr can be ignored if there is no capacitor 40, the amplification factor of the noise in the feedback loop can be expressed as (Zc+Zw)/Zw.

In the above case, the ratio of the impedance Zc of the counter electrode 91 and the impedance Zw of the working electrode 93 is calculated as Zc/Zw≈(1/Cc)/(1/Cw)=Cw/Cc=7 μF/2.8 μF=2.5. Therefore, the amplification factor of the noise in the feedback loop in the absence of the capacitor 40 is (Zc+Zw)/Zw=(1+2.5)/1=3.5.

On the other hand, in the present disclosure, the capacitor 40 is connected to the first node 11 which is the output of the operational amplifier 30 and the second node 12 which is the inverting input (−IN) of the operational amplifier 30. In the feedback loop, the capacitor 40 is arranged in parallel with a path from the first node 11 which is the output (OUT) of the operational amplifier 30, via the counter electrode 91, the solution 95, and the reference electrode 92, back to the second node 12 which is the inverting input (−IN) of the operational amplifier 30. Therefore, the feedback amount of the feedback loop is increased as compared to when there is no capacitor 40. Thus, the noise power appearing at the counter electrode 91 via the first node 11 is reduced, and it is possible to improve the measurement accuracy of the minute current.

Figure 10:
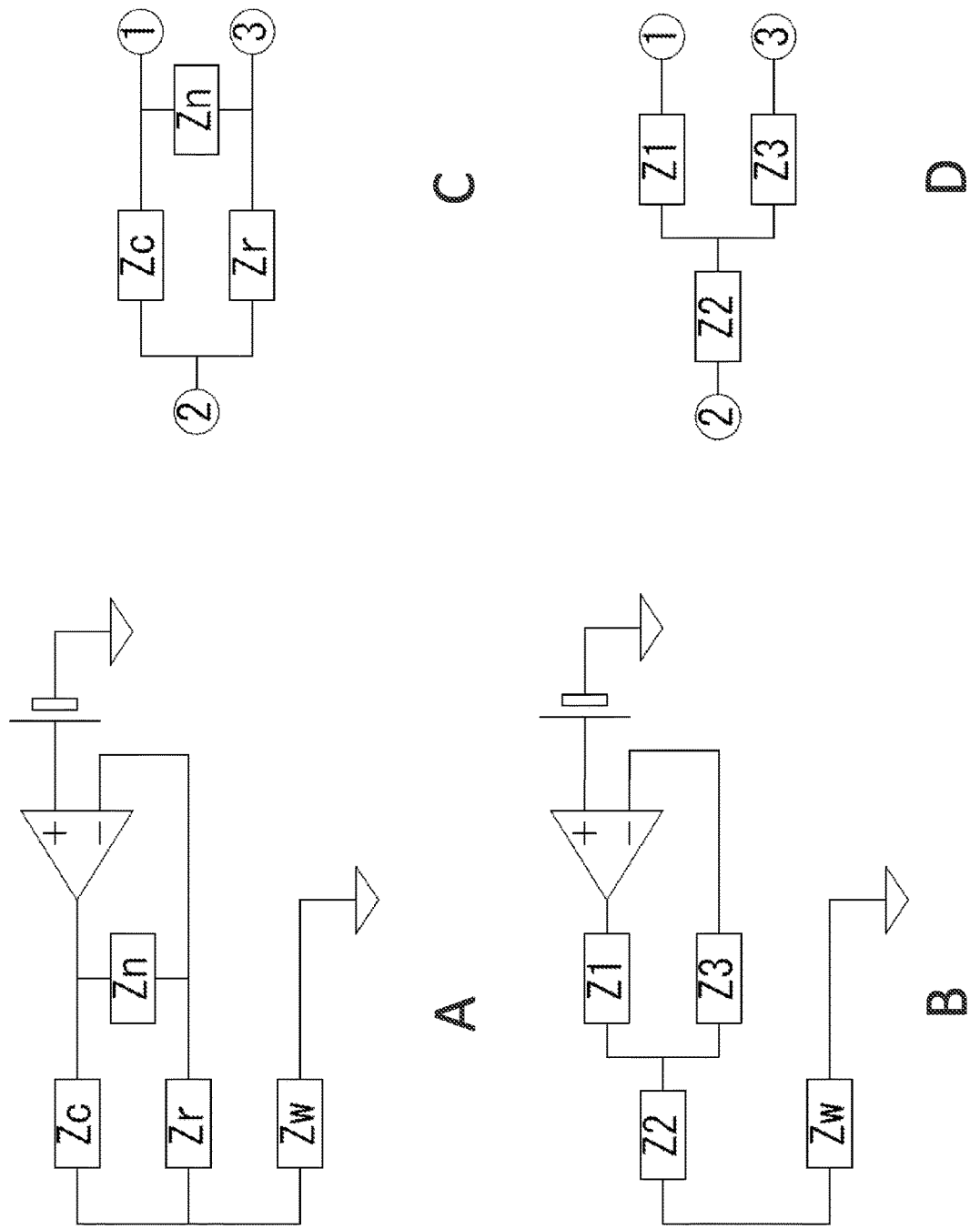
FIG. 10 illustrates a circuit diagram for explaining the conversion of the electrical equivalent circuit.

When the feedback amount of the feedback loop becomes large, the amplification factor of the noise becomes small, which can be understood by considering as follows. First, the connection of Zc, Zr, and the impedance Zn of and the capacitor 40 is regarded as a π-type connection (FIG. 10A), which can be converted into T-type connection (FIG. 10B). More specifically, π-type connection of Zc, Zr, Zn shown in FIG. 10C can be converted to T-type connection of Z1, Z2, Z3 shown in FIG. 10D. Here, they can be expressed as follows: $Z1=(Zc \times Zn)/(Zr+Zn+Zc)$, $Z2=(Zr \times Zc)/(Zr+Zn+Zc)$, $Z3=(Zn \times Zr)/(Zr+Zn+Zc)$. The T-type connection of Z1, Z2, and Z3 shown in FIG. 10B can be similarly expressed. Then, assuming that the operational amplifier 30 is arranged and the input impedance of the operational amplifier 30 is sufficiently large, Z3 can be ignored, and therefore the feedback amount of the feedback loop can be expressed as $(Z2+Zw)/(Z1+Z2+Zw)$, and the amplification factor of the noise can be expressed as $(Z1+Z2+Zw)/(Z2+Zw)$. Here, if the impedance Zn of capacitor 40 is sufficiently small relative to the impedance Zc at the counter electrode 91, then $Z2 \gg Z1$. Therefore the amplification rate of noise becomes $(Z1+Z2+Zw)/(Z2+Zw) \sim (Z2+Zw)/(Z2+Zw)=1$. Alternatively, it may be understood that the amplification factor of the non-inverting amplifier of the feedback loop is reduced, the amplification factor of the integrated physical noise present in the non-inverting input (+IN) of the operational amplifier 30 is reduced.

When the capacitance Cn of the capacitor 40 is larger than the capacitance Cc of the interface of the counter electrode 91, the feedback amount increases. For example, when the capacitances Cc and Cw of the counter electrode 91 and the working electrode 93 described above are used as they are and the capacitance Cn of the capacitor 40 is 100 μF, most of the feedback is performed through the capacitor 40, so that the feedback amount becomes almost 1 and the noise is not amplified. That is, as compared with the case without the capacitor 40 it leads to 3.5 times of the noise reduction.

Noise caused by external noise with a relatively high frequency can be reduced by averaging in accordance with countermeasures for shielding and ground. However, noise with relatively low frequency cannot be expected to be reduced by techniques such as averaging. For example, physical noise cannot be reduced in the shield or ground because it is inherent in the parts. In addition, attempting to reduce physical noise with low frequency by averaging may also reduce the original signal. Among physical noises, flicker noise, which increases inversely proportionally to the frequency, is the dominant noise at low frequencies. Flicker noise in the vicinity of the time constant of the electrochemical reaction is very difficult to remove by conventional methods.

On the other hand, the electric circuit including the capacitor 40 and the feedback circuit thereof can remarkably enhance the effect of noise reduction in the frequency range of, for example, about 0.01 Hz to 10 Hz. Alternatively, the electrical circuit and its feedback circuit having the capacitor 40, for example, can increase the feedback amount of noise having a frequency of about 10 Hz from 0.01 Hz, and thus the amplification of noise in the feedback circuit is suppressed. In electrochemical measurements, chemical reactions may take from 0.1 seconds to about 1 minute or more. Thus, the electrical circuit including the capacitor 40 of the present disclosure can improve the accuracy of the electrochemical measurement.

Figure 8:
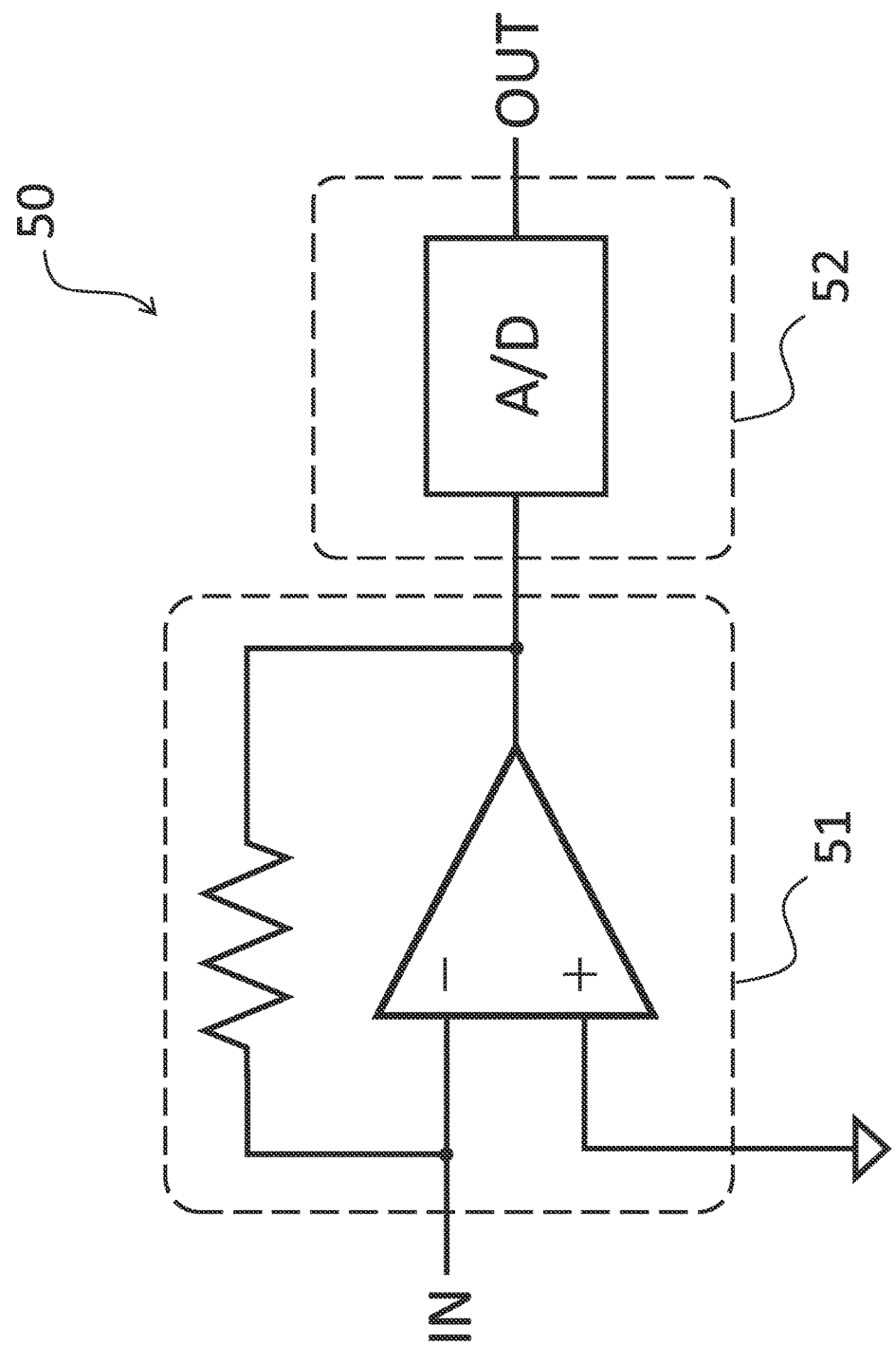
FIG. 8 illustrates an example of a typical circuit constituting the current measuring circuit.

As shown in FIG. 8, the current measuring circuit 50 may be provided with a current-voltage conversion circuit 51. In some embodiments, the current-voltage conversion circuit 51 may be configured using an operational amplifier and a resistor. At this time, the inverting input of the operational amplifier is a virtual ground. The input impedance of the third node 13 is low and can be considered zero. Measuring device 1 may have an analog-to-digital (A/D) conversion circuit 52 inside the current-voltage conversion circuit 50 (FIG. 8) or outside thereof. In the current measuring circuit 50 shown in FIG. 8, the current signal from the working electrode 93 is current-voltage converted by the current-voltage conversion circuit 51, converted into digital data by the A/D converter 52, and output as a digital signal to the outside of the electric circuit 10.

The counter electrode 91 is an electrode having a predetermined voltage difference between it and the working electrode 93. The voltage difference may be determined according to the type of electrode used for measurement or the substance to be measured. In some embodiments, when a molecular recognition film is provided on an electrode or an electrode surface, a voltage as high as possible may be applied within a range in which an excessive load is not applied to the molecular recognition film. The potential difference between the counter electrode 91 and the solution 95 changes in accordance with the amount of current flowing. Therefore, in order to keep the potential of the solution 95 at a predetermined value, the potential of the solution is measured by the reference electrode 92, and the potential of the counter electrode 91 is controlled by the feedback circuit.

In some embodiments, a molecular recognition film that specifically reacts with a substance to be measured is provided on a surface of the working electrode 93 (not shown) The molecular recognition film may include a polymer film. The polymer film may be, for example, a biomolecule such as an antigen, an antibody, an enzyme, or the like, a self-assembled monomolecular film (SAM: Self-Assembled Monolayer), a polymer film such as a molecular template polymer (MIP: Molecular Imprinted Polymer), or the like, depending on the substance to be measured. When the molecular recognition film reacts with the substance to be measured in an environment in which a voltage from the counter electrode 91 is applied, a current is generated. It is considered, for example, that when the substance to be measured is decomposed in the molecular recognition film, a current is generated by the transfer of electrons such as redox. It is considered that when the substance to be measured is bound in the molecular recognition film, a current is generated by a change in the surface charge. It is considered that some change in the substance to be measured in the molecular recognition film is detected as an electric signal through the working electrode. The above mechanisms are examples and presumptive, and do not limit the present disclosure, and other mechanisms may also be possible.

The shield 60 is made of an electrically conductive material including, for example, a metal. In some embodiments, the shield 60 may block noise entering from outside the equipment. In some embodiments, by setting the shield to the same as the ground potential, it is also possible to reduce the noise generated in the internal circuit such as commercial power supply noise and switching noise.

At measurements, the voltage generating circuit 20 generates a reference voltage Vref, and supply this to the operational amplifier 30. The operational amplifier 30 performs control of the output voltage so that the reference electrode 92 is at the reference voltage Vref. At the working electrode 93, a chemical reaction is performed.

EXAMPLE 1

Below, one embodiment included in the present disclosure will be described. As the counter electrode 91, a platinum electrode having an area of about 4 square millimeters was used. As the working electrode 93, a platinum electrode of about 10 square millimeters was used, and a fructosylamino acid oxidase (FAOD) enzymatic film for measuring glycoalbumin was formed on this surface. As the reference electrode 92, a platinum electrode of about 2 square millimeters was used, and silver chloride was disposed on the surface of the platinum electrode.

Figure 2:
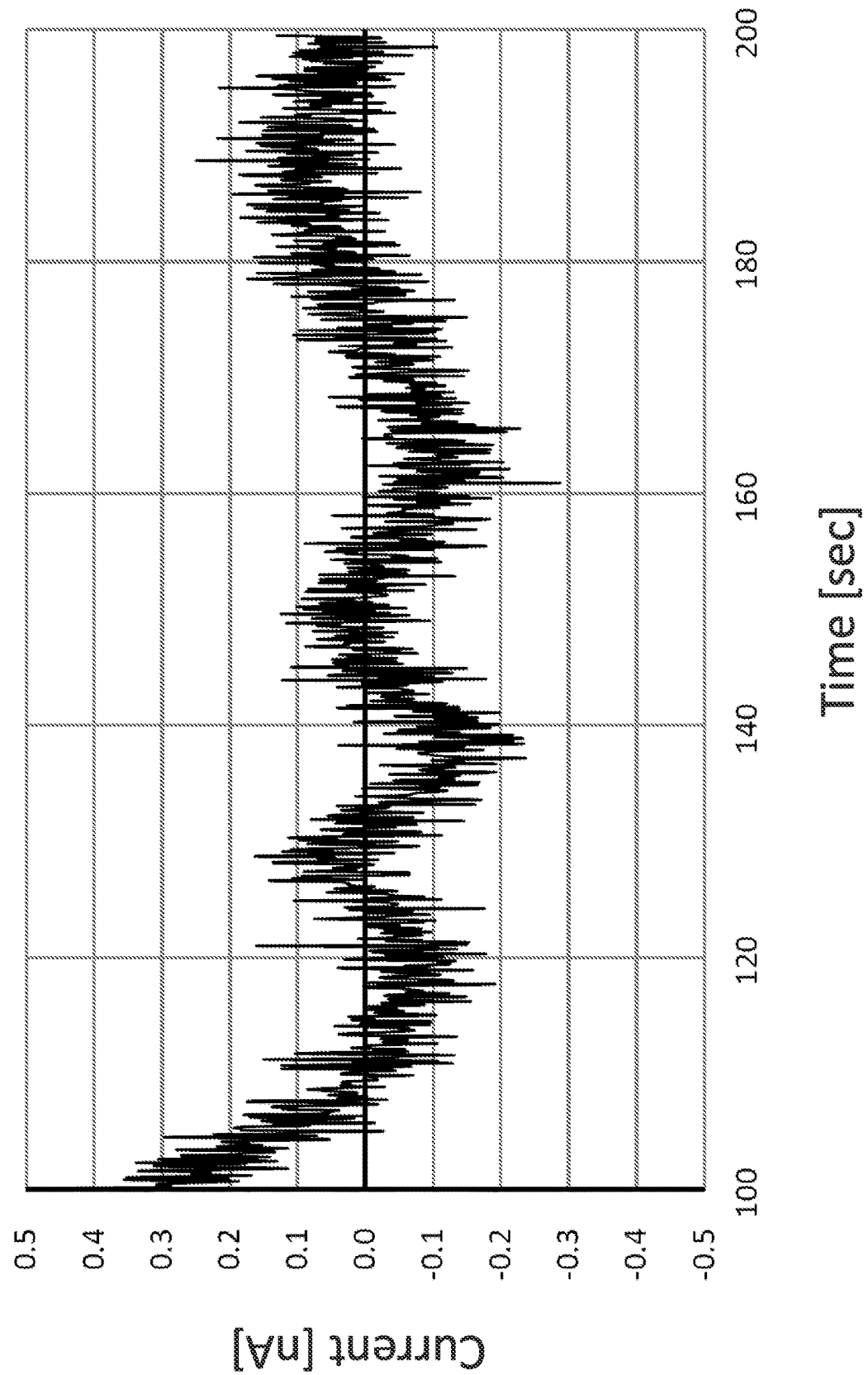
FIG. 2 illustrates a waveform diagram showing an example of a current measured without noise countermeasure.
Figure 3:
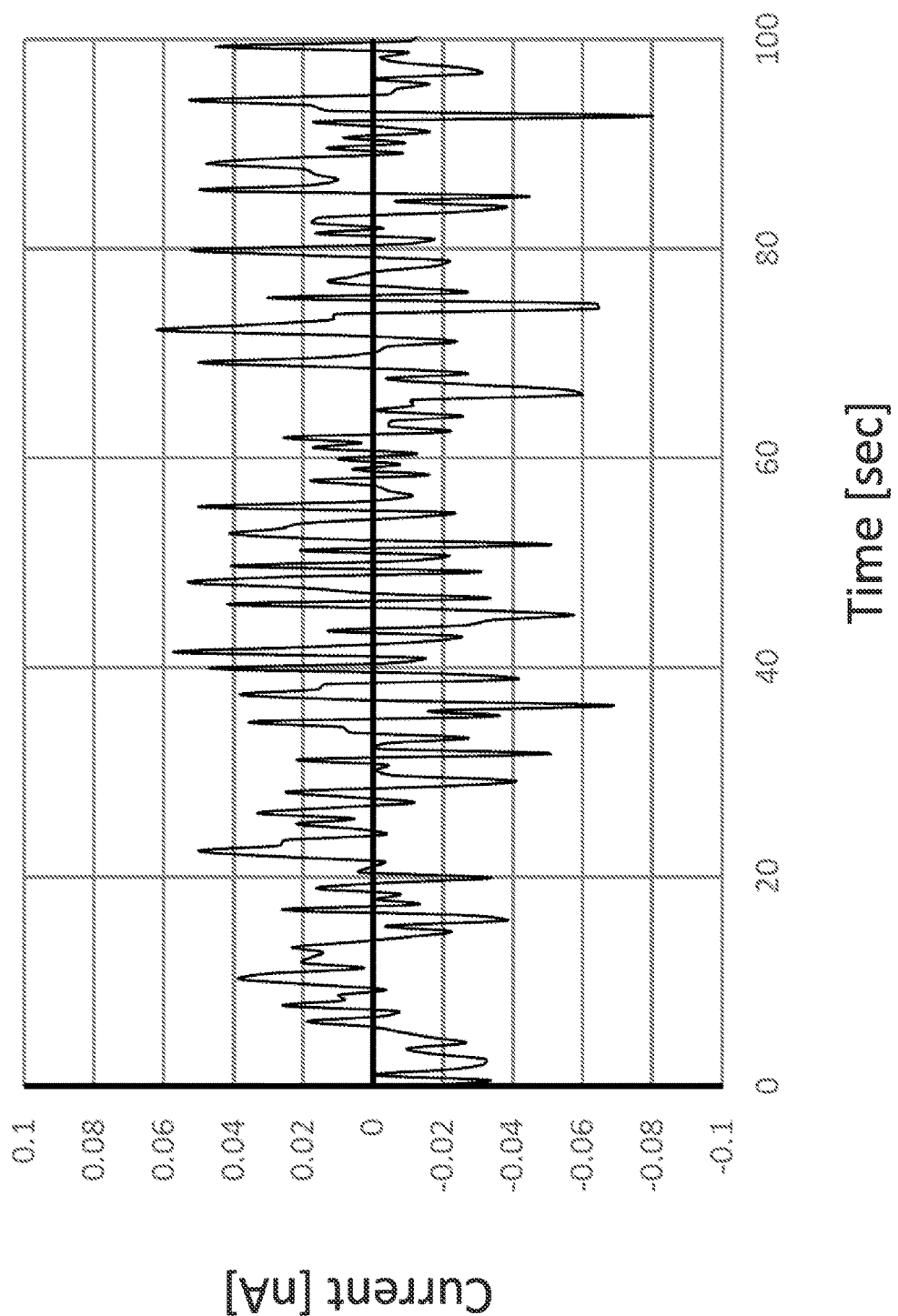
FIG. 3 illustrates a waveform diagram showing an example of a current measured by performing only countermeasures against external noise.
Figure 4:
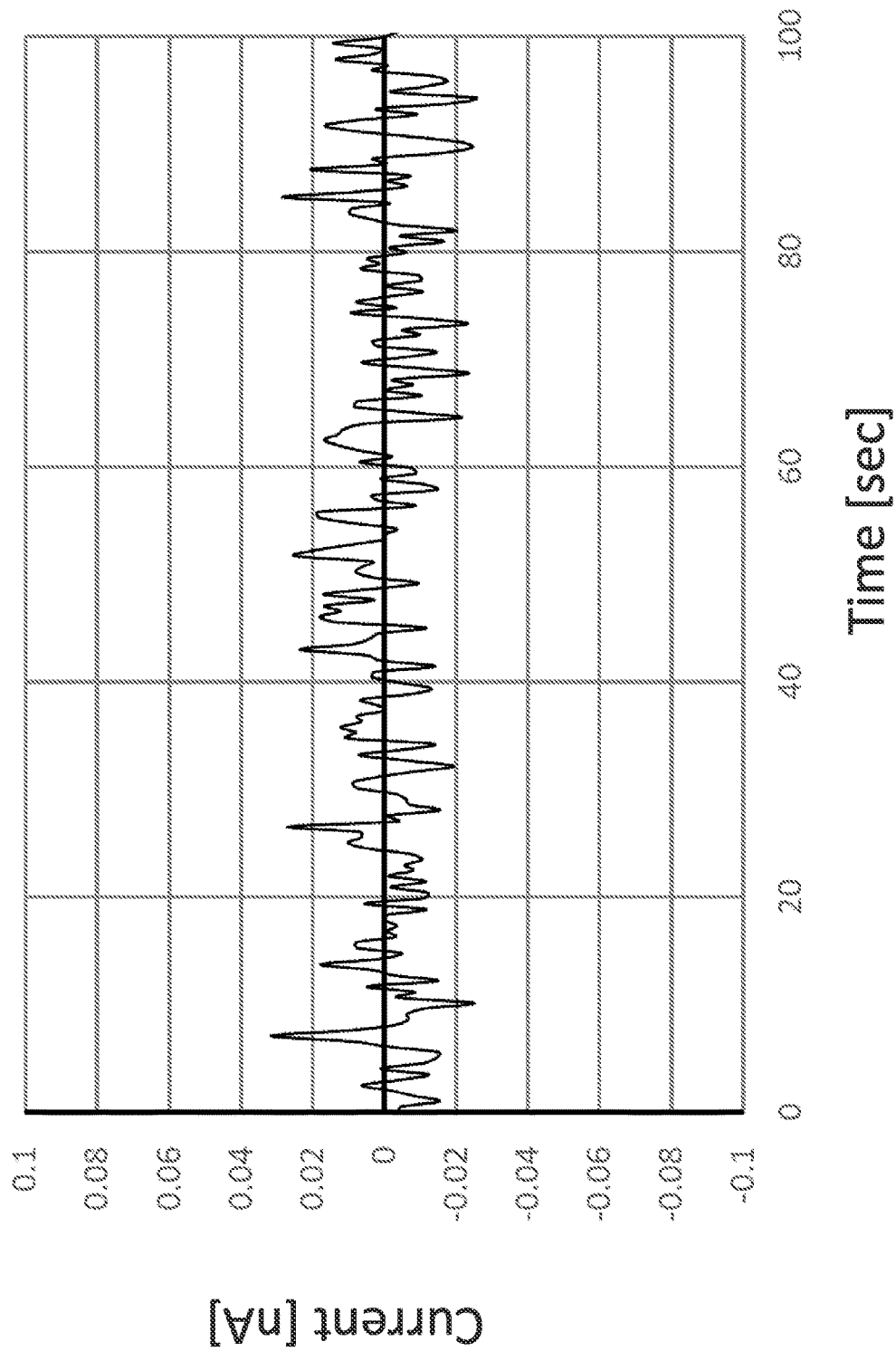
FIG. 4 illustrates a waveform diagram showing an example of a current measured by performing noise countermeasure according to the first embodiment.

In a state in which a voltage of 450 mV was applied between the counter electrode 91 and the working electrode 93, the measurement was carried out with the 3 electrodes being immersed in a 300 mM N-[tris (hydroxymethyl)-methyl]-2-aminoethanesulfonic acid (TES) solution which is a good buffer. The noise waveform at that time is shown in FIGS. 2, 3 and 4. FIG. 2 shows a noise waveform measured without the noise countermeasure according to the present disclosure. FIG. 3 shows the noise waveform when taking measures to reduce external noise by performing such shielding and appropriate ground arrangement. FIG. 4 shows a noise waveform when placing a capacitor of 10 µF as the capacitor 40 according to the present disclosure.

As shown in FIG. 2, noise of the order of 0.7 nA (nanoampere) p-p (peak to peak) was observed when no noise countermeasures were taken. As shown in FIG. 3, noise of about 0.12 nAp-p was observed when measures to reduce external noise were taken. The influence of external noise almost disappeared, and the physical noise became dominant for the observed noise. However, the amplification effect in the feedback loop was observed. As shown in FIG. 4, noise was reduced to about 0.04 nAp-p when an electric circuit including a noise reduction capacitor was used.

It was confirmed that the amplification effect of noise was reduced.

Next, other examples included in the present disclosure will be described.

EXAMPLE 2

In this example, TES containing no glycoalbumin was introduced into the container 90 to immerse the counter electrode 91, the reference electrode 92, and the working electrode 93. Thereafter it was replaced by 1 mg/mL of glycoalbumin dissolved in TES.

Figure 5:
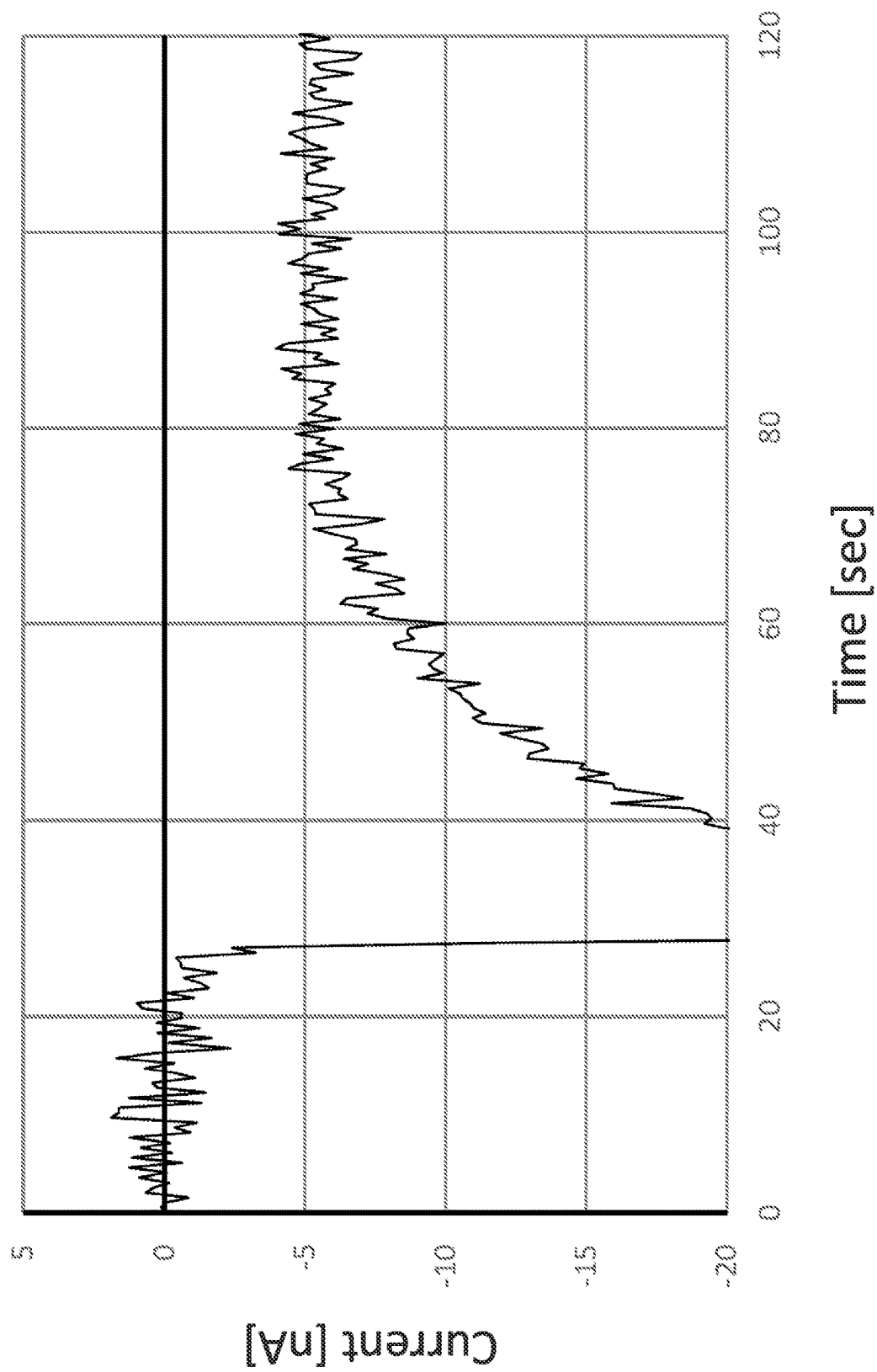
FIG. 5 illustrates a waveform diagram showing an example of a current measured by performing only countermeasures against external noise.
Figure 6:
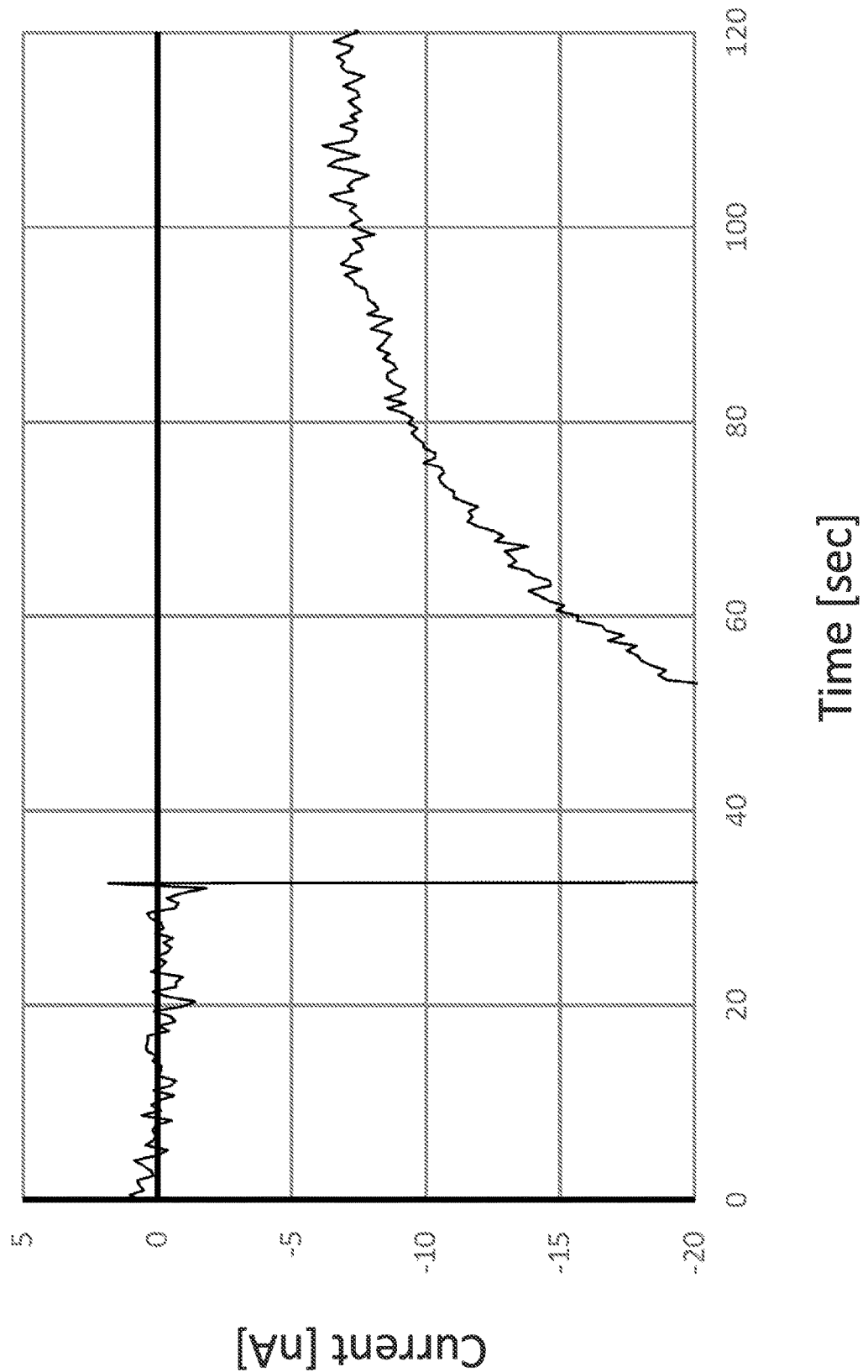
FIG. 6 illustrates a waveform diagram showing an example of a current measured by performing noise countermeasure according to the first embodiment.

The current waveforms measured for this solution under the same conditions as in Example 1 are shown in FIGS. 5 and 6. FIG. 5 shows an example of a current waveform when taking measures to reduce external noise by performing such shielding and appropriate ground arrangement. FIG. 6 shows a current waveform when placing a capacitor of 10 vµF as a capacitor 40.

FIGS. 5 and 6 show the replacement of solutions at the 28-second and 32-second time points in each graph. During the solution exchange, the current value increased rapidly. (In these figures, the downward direction of the graph means an increase in current in relation to the measurement system.) Thereafter, at around 80 seconds, the current stabilized. It is considered that such a peak current is generated by a factor other than a desired chemical reaction, such as the formation of an electric double layer or the variation of the concentration distribution of ions in the solution or the like. This peak current makes it difficult to measure the current corresponding to the chemical reaction to be measured. Therefore, it is preferable to measure a stable current after the peak current or the rapid change of the current has disappeared.

For example, the concentration of glycoalbumin in tears of about 10 µL is about 1 mg/mL. Therefore, quantification of glycoalbumin in tears requires accurate measurement of this degree of current. The current value at the time of stability is about 5 to 10 nA. It is required to measure this value with an accuracy of 1% units, i.e. an accuracy of 0.05 nA to 0.1 nA or so. In the measurement of FIG. 5, it is almost impossible to ensure an accuracy of 1% of the current value. On the other hand, in the measurement of FIG. 6, it is possible to reduce the influence of noise to 1% or less. In addition, time averaging may be used. This can further increase the measurement accuracy.

As in the case of the present embodiment, when the substance to be measured is added to the solution not containing the substance to be measured, the current flowing from the counter electrode to the working electrode changes, and the potential of the counter electrode 91 changes accordingly. Since the potential of the reference electrode 92 is constant, the potential difference applied across the capacitor 40 is changed. Since this change requires the injection of charge, the capacitor 40 needs to be charged during the measurement. At this time, the charge injected into the capacitor 40 only passes through the second node 12 from the reference electrode 92. The current injected from reference electrode 92 is limited by the electrical resistance of reference electrode 92. That is, the injection time of charge into the capacitor 40 is determined by the electrical resistance of the reference electrode 92 and the capacitance of the capacitor 40.

For example, as in this embodiment, when the capacitance of the capacitor 40 is 10 µF, and the electrical resistance of the reference electrode 92 is about 2 MO, the time constant of charging of the capacitor 40 is 20 seconds. Therefore, this configuration, while achieving an effect of suppressing noise, it is possible to avoid or reduce the waiting time of charging of the capacitor 40 which is a large hindrance to the measurement. In other words, it is possible to achieve both the improvement of the measurement accuracy of the minute current, and the suppression of the measurement time.

In another embodiment, the capacitance of the capacitor 40 may be 100 µF or larger. The impedance Zn of the capacitor 40 is further reduced, further improving the feedback amount of noise, and further suppressing the amplification of noise. Thus, it is possible to further improve the measurement accuracy of the minute current.

SECOND EMBODIMENT

Next, another embodiment (second embodiment) of the present disclosure will be described with reference to FIG.

7. Hereinafter, the description of the overlapping portions with the aforementioned embodiments will be omitted in principle.

Figure 7:
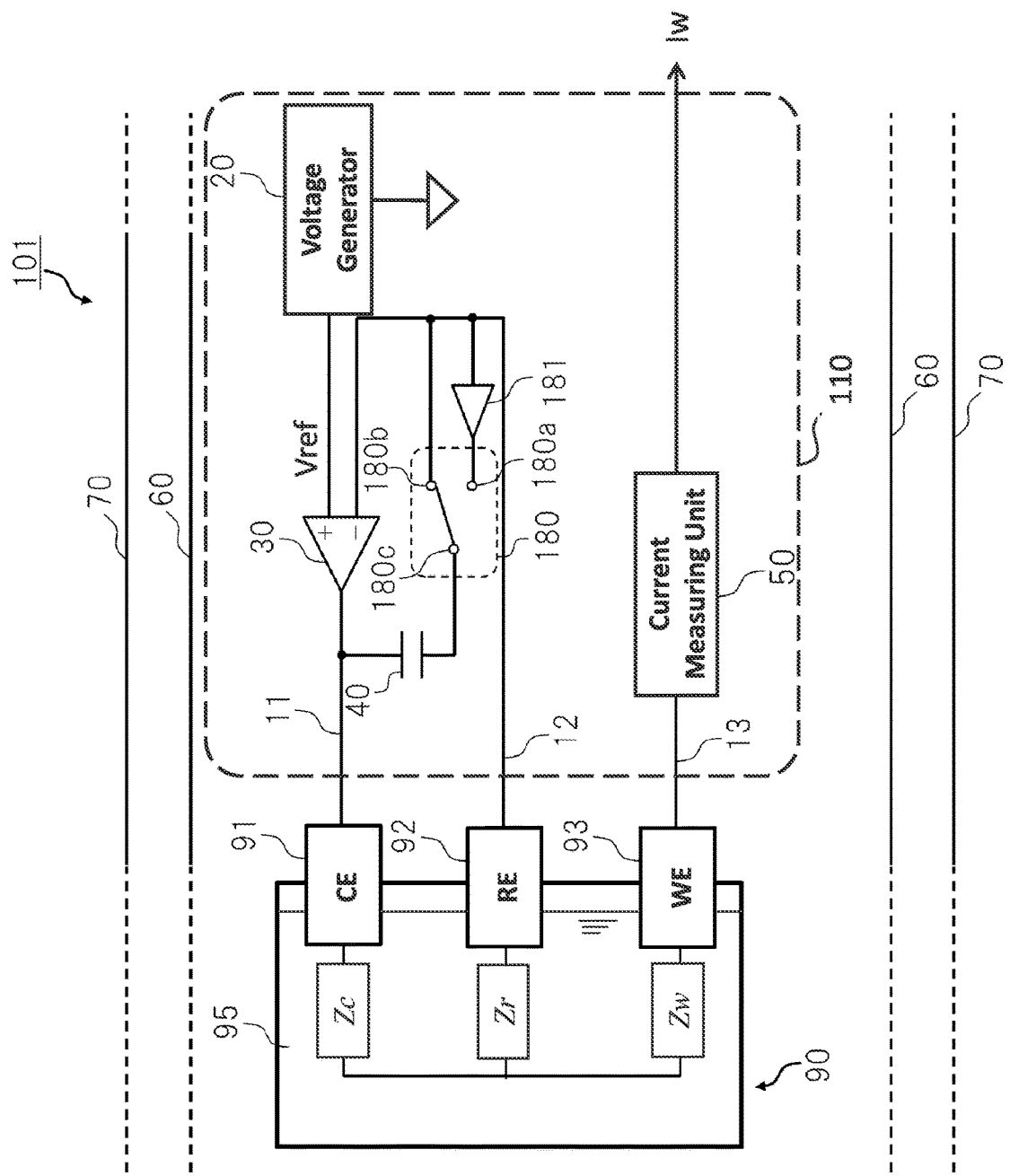
FIG. 7 illustrates a circuit block diagram showing an example of a configuration of a measurement device according to the second embodiment.

FIG. 7 is a circuit block diagram showing an example of the configuration of the measurement apparatus according to the second embodiment. The measuring device 101 shown in FIG. 7 includes an electric circuit 110, a container 90 containing a solution 95, a counter electrode 91, a reference electrode 92, a working electrode 93, a shield 60, and a housing 70. The electric circuit 110 includes a voltage generating circuit 20, an operational amplifier 30, a capacitor 40, a switch (switch circuit) 180, and a buffer circuit 181. In some embodiments, the electrical circuit 110 may include a voltage generating circuit 20, a operational amplifier 30, a capacitor 40, a current measuring circuit 50, and a capacitor charging circuit (not shown). The time to charge the capacitor 40 by the capacitor charging circuit may be less than or equal to any value of 1 second, 5 seconds, 10 seconds, 30 seconds, 1 minute, 2 minutes, 3 minutes, 4 minutes, 5 minutes, 10 minutes, 15 minutes, 30 minutes, 60 minutes.

The capacitor 40 shown in FIG. 7 is provided between the first node 11 and the switch 180. That is, the capacitor 40 has one end connected to the output (OUT) of the operational amplifier and the first node 11, and the other end connected to the output terminal 180c of the switch circuit 180.

The switch 180 is a circuit block having a first input terminal 180a, a second input terminal 180b, and an output terminal 180c. The switch 180 has a control unit (not shown), which can switch the connection of the two input terminals by the control unit. The first input terminal 180a is connected to the output terminal of the buffer circuit 181. The second input terminal 180b is connected to the inverting input (−IN) of the operational amplifier 30 and the reference electrode 92, that is, to the second node 12. The output terminal 180c is connected to one end of the capacitor 40. The switch 180 can switch the connection destination of the capacitor 40 by switching the connection of the input terminal.

Buffer circuit 181 is a circuit that receives the input voltage at a high impedance, and outputs the same voltage as the input voltage at a low impedance. The buffer circuit 181 shown in FIG. 7 is connected at its output terminal to the first input terminal 180a of the switch circuit 180. The input terminal is connected to the inverting input (−IN) and to the reference electrode 92, i.e. to the second node 12. When the switch 180 is connected to the first input terminal 180a, the buffer circuit 181 receives the voltage of the reference electrode 92 and the second node 12 with a high impedance, and charges the capacitor 40 with a low impedance. The buffer circuit 181 may be a voltage follower using an operational amplifier. However, the configuration of the buffer circuit 181 is not limited thereto and may be different.

The capacitance of the capacitor 40 may be greater than the interface capacitance of the counter electrode 91 and the interface capacitance of the reference electrode 92. In this case, the charging time of the capacitor 40 may be longer than the time until the chemical reaction becomes stable. The capacitor 40 may also delay the progress of the chemical reaction. Electrochemical measurements cannot be performed correctly while the capacitor 40 is being charged. Therefore, the time while the capacitor 40 is charged is a waiting time. Therefore, it is necessary to set the measurement time longer than when there is no capacitor 40, in other words, it is necessary to set the measurement time sufficiently long including the waiting time for charging of the capacitor 40. For example, if the capacitance of the capacitor 40 is 10 μF, 100 μF, and the resistive component at the interface of the reference electrode 92 is 2 MO (megohms), the time constant calculated as a simple CR product is 20 seconds, 200 seconds, respectively. These time constants may affect chemical and biochemical reactions.

In addition, the reduction of the amplification factor of the noise and the minimization of the influence on the reaction and the shortening of the measurement time can become a trade-off relationship. Thus, even in an optimized configuration, both noise reduction effects and measurement times can be sacrificed a little. Furthermore, depending on the electrode used, the capacitance of the optimum noise reduction capacitor is different. For example, since the electrode to be used may be different depending on the substance to be measured, the electrode to be used, the molecular recognition film, the concentration of the measurement substance in the solution or the solution at the time of measurement, and the concentration to be measured, it may become necessary to replace the capacitor for reducing noise.

In contrast, the electric circuit 110 having the buffer circuit 181 and the switch 180 as in the present embodiment, potentially achieves the following effects. That is, before the chemical reaction is stabilized, that is, before the measurement is started, the output terminal 180c and the input terminal 180a of the switch 180 are connected in accordance with a signal from the control unit. Thus, the switch 180 connects the output terminal of the capacitor 40 and the buffer circuit 181. Therefore, the capacitor 40 can be rapidly charged to a predetermined voltage by the configuration of the electric circuit including the buffer 181 until the chemical reaction is stabilized. During charging, the capacitor 40 does not become a component of the feedback loop and therefore does not affect the chemical and biochemical reactions nor the convergence time of the feedback circuit. In some embodiments, the output impedance of the buffer circuit 181 can be smaller than or equal to 1Ω, which allows the charging time of the capacitor 40 to be smaller than or equal to 100 μsec (microseconds). For example, in the embodiment shown in FIG. 5 or FIG. 6, the chemical reaction settled in about 1 minute. In such a case, if the charging time is about 1 second to a few seconds, it is not a major problem for measurements. If the chemical reaction settles in about 5 seconds, the time constant of the circuit can be 100 msec.

When the chemical reaction becomes stable, the control unit switches the switch 180, to connect the capacitor 40 and the second node 12. At this time, the capacitor 40 is charged to the same voltage as the voltage of the second node 12 by the buffer 181. Therefore, there is no need to re-converge the feedback circuit by switching, achieving noise reduction at the time of measurement as one effect.

The present disclosure includes, but is not limited to, the following embodiments:

1. An electrical circuit used for an electrochemical measurement of a solution, comprising:
   a voltage generating circuit;
   an operational amplifier having an output (OUT), a non-inverting input (+IN), and an inverting input (−IN);
   the output (OUT) being configured to be connected to a counter electrode (CE) in contact with the solution,
   the inverting input (−IN) being configured to be connected to a reference electrode (RE) in contact with the solution,
   the non-inverting input (+IN) being connected to the voltage generating circuit;
   a capacitor connected between the output (OUT) and the inverting input (−IN), the capacitor having a capacitance of 1 μF or greater; and a current measuring circuit configured to be connected to a working electrode (WE) in contact with the solution.

2. The electric circuit according to Embodiment 1, wherein the capacitance of the capacitor is 10 μF or greater.

3. The electric circuit according to Embodiment 2, wherein the capacitance of the capacitor is 100 μF or greater.

4. The electrical circuit of any one of Embodiments 1 to 3, wherein the capacitance of the capacitor is greater than the capacitance of an equivalent circuit at the interface of the counter electrode under measurement.

5. An electrical circuit used for an electrochemical measurement of a solution, comprising:
a voltage generating circuit;
a current measuring circuit configured to be connected to a working electrode (WE) in contact with the solution;
an operational amplifier having an output (OUT), a non-inverting input (+IN), an inverting input (−IN),
the output (OUT) being configured to be connected to a counter electrode (CE) in contact with the solution,
the inverting input (−IN) being configured to be connected to a reference electrode (RE) in contact with the solution, and
the non-inverting input (+IN) is connected to the voltage generating circuit;
a capacitor having a capacitance of 1 μF or greater;
a switch circuit having a first input terminal, a second input terminal and an output terminal; and
a buffer circuit having an input terminal and an output terminal,
wherein the capacitor is connected to the output of the operational amplifier at one end (OUT), and connected to the output terminal of the switch circuit at the other end,
wherein the switch circuit is connected to the output terminal of the buffer circuit at the first input terminal, and connected between the inverting input (−IN) of the operational amplifier at the second input terminal, and
wherein the buffer circuit is connected to the inverting input (−IN) of the operational amplifier at the input terminal.

6. A device for an electrochemical measurement of a solution, comprising:
a counter electrode (CE) configured to contact the solution;
a reference electrode (RE) configured to contact the solution;
a working electrode (WE) configured to contact the solution;
a voltage generating circuit;
an operational amplifier having an output (OUT), a non-inverting input (+IN), and an inverting input (−IN);
the operational amplifier being connected to the counter electrode (CE) at the output (OUT), connected to the reference electrode (RE) at the inverting input (−IN), and connected to the voltage generating circuit at the non-inverting input (+IN);
a capacitor connected between the output of the operational amplifier (OUT) and the inverting input (−IN), the capacitor having a capacitance of 1 μF or greater; and
a current measuring circuit connected to the working electrode (WE).

7. The electrochemical measurement device according to Embodiment 6,
wherein the solution contains a substance to be measured, the device further comprising a molecular recognition film that is provided on a surface at least to come in contact with the solution of the working electrode, and that specifically reacts with the substance to be measured.

8. A device for an electrochemical measurement of a solution, comprising:
a counter electrode (CE) configured to contact the solution;
a reference electrode (RE) configured to contact the solution;
a working electrode (WE) configured to contact the solution;
a voltage generating circuit;
a current measuring circuit connected to the working electrode (WE);
an operational amplifier having an output (OUT), a non-inverting input (+IN), and an inverting input (−IN),
the output (OUT) being connected to the counter electrode (CE),
the inverting input (−IN) being connected to the reference electrode (RE), and
the non-inverting input (+IN) being connected to the voltage generating circuit;
a capacitor having a capacitance of 1 μF or greater;
a switch circuit having a first input terminal, the second input terminal and the output terminal; and
a buffer circuit having an input and an output,
wherein the capacitor is connected to the output of the operational amplifier (OUT) and the counter electrode (CE) at one end, and connected to the output terminal of the switch circuit at the other end,
wherein the switch circuit is connected to the output terminal of the buffer circuit at the first input terminal, and connected to the inverting input of the operational amplifier (−IN) and the reference electrode (RE) at the second input terminal,
wherein the buffer circuit is connected to the inverting input (−IN) of the operational amplifier and the reference electrode (RE) at an input terminal.

9. The electrochemical measurement device according to Embodiment 8,
wherein the solution contains a substance to be measured, the device further comprising a molecular recognition film that is provided on a surface at least to come in contact with the solution of the working electrode, and that specifically reacts with the substance to be measured.

While several embodiments and examples of the present disclosure have been described above, these embodiments and examples illustrate the present disclosure.

For example, each of the above-described embodiments has been described in detail in order to explain the present invention easily, and a circuit may be added as necessary.

It is intended that the appended claims cover numerous modifications to the embodiments without departing from the spirit and scope of the present disclosure.

Accordingly, the embodiments and examples disclosed herein have been shown by way of example and should not be considered as limiting the scope of the present disclosure.

1,101 . . . Measuring device
10,110 . . . Electric circuit
11,12,13 . . . Node
20 . . . Voltage generator circuit
30 . . . Feedback circuit
40 . . . Capacitor
50 . . . Current measurement circuit
51 . . . Current-voltage conversion circuit
52 . . . Analog-to-digital conversion circuits 60 . . . Shield
70 . . . Housing
90 . . . Container
91 . . . Counter electrode
92 . . . Reference electrode
93 . . . Working electrode
95 . . . Solution
180 . . . Switch
181 . . . Buffer circuit

What is claimed is:

1. An electrical circuit used for an electrochemical measurement of a solution, comprising:
   a voltage generating circuit;
   a current measuring circuit configured to be connected to a working electrode (WE) in contact with the solution;
   an operational amplifier having an output (OUT), a non-inverting input (+IN), an inverting input (−IN),
   the output (OUT) being configured to be connected to a counter electrode (CE) in contact with the solution,
   the inverting input (−IN) being configured to be connected to a reference electrode (RE) in contact with the solution, and
   the non-inverting input (+IN) is connected to the voltage generating circuit;
   a capacitor having a capacitance of 1 µF or greater;
   a switch circuit having a first input terminal, a second input terminal and an output terminal; and
   a buffer circuit having an input terminal and an output terminal,
      wherein the capacitor is connected to the output of the operational amplifier at one end (OUT), and connected to the output terminal of the switch circuit at the other end, wherein the switch circuit is connected to the output terminal of the buffer circuit at the first input terminal, and connected between the inverting input (−IN) of the operational amplifier at the second input terminal, and
      wherein the buffer circuit is connected to the inverting input (−IN) of the operational amplifier at the input terminal.

2. The electrical circuit of claim 1, wherein the capacitance of the capacitor is 10 µF or greater.

3. The electrical circuit of claim 1, wherein the capacitance of the capacitor is 100 µF or greater.

4. The electrical circuit of claim 1, wherein the capacitance of the capacitor is greater than the capacitance of an equivalent circuit at an interface of the counter electrode under measurement.

5. A device for an electrochemical measurement of a solution, comprising:
   a counter electrode (CE) configured to contact the solution;
   a reference electrode (RE) configured to contact the solution;
   a working electrode (WE) configured to contact the solution;
   a voltage generating circuit;
   a current measuring circuit connected to the working electrode (WE),
   an operational amplifier having an output (OUT), a non-inverting input (+IN), and an inverting input (−IN),
   the output (OUT) being connected to the counter electrode (CE),
   the inverting input (−IN) being connected to the reference electrode (RE), and
   the non-inverting input (+IN) being connected to the voltage generating circuit;
   a capacitor having a capacitance of 1 µF or greater;
   a switch circuit having a first input terminal, a second input terminal and an output terminal; and
   a buffer circuit having an input and an output,
   wherein the capacitor is connected to the output of the operational amplifier (OUT) and the counter electrode (CE) at one end, and connected to the output terminal of the switch circuit at the other end,
   wherein the switch circuit is connected to the output terminal of the buffer circuit at the first input terminal, and connected to the inverting input of the operational amplifier (−IN) and the reference electrode (RE) at the second input terminal, and
   wherein the buffer circuit is connected to the inverting input (−IN) of the operational amplifier and the reference electrode (RE) at an input terminal.

6. The device of claim 5,
   wherein the solution contains a substance to be measured,
   the device further comprising a molecular recognition film that is provided on a surface at least to come in contact with the solution of the working electrode, and that specifically reacts with the substance to be measured.

7. The device of claim 5, wherein the capacitance of the capacitor is 10 µF or greater.

8. The device of claim 5, wherein the capacitance of the capacitor is 100 µF or greater.

9. The device of claim 5, wherein the capacitance of the capacitor is greater than the capacitance of an equivalent circuit at an interface of the counter electrode under measurement.

* * * * *